(12) United States Patent
Varga et al.

(10) Patent No.: US 8,119,371 B2
(45) Date of Patent: Feb. 21, 2012

(54) **PROCESS FOR THE PREPARATION OF POLYMYXIN B EMPLOYING (PAENI) *BACILLUS POLYMYXA***

(75) Inventors: Ivan Varga, Hlohovec (SK); Katarina Vrúblová, Banská Bystrica (SK); Ludmila Kovácová, Lucatin (SK); Jana Kluková, Banská Bystrica (SK)

(73) Assignee: Biotika A.S., Lupca (SK)

( * ) Notice: Subject to any disclaimer, the term of this patent is extended or adjusted under 35 U.S.C. 154(b) by 551 days.

(21) Appl. No.: 12/304,321

(22) PCT Filed: May 21, 2007

(86) PCT No.: PCT/SK2007/050011
§ 371 (c)(1),
(2), (4) Date: Dec. 11, 2008

(87) PCT Pub. No.: WO2007/145602
PCT Pub. Date: Dec. 21, 2007

(65) Prior Publication Data
US 2009/0197305 A1    Aug. 6, 2009

(30) Foreign Application Priority Data
Jun. 15, 2006 (SK) .................................. 0090-2006

(51) Int. Cl.
*C12P 21/04* (2006.01)
(52) U.S. Cl. .................................................... 435/71.3
(58) Field of Classification Search .................. None
See application file for complete search history.

(56) References Cited

U.S. PATENT DOCUMENTS

| | | | |
|---|---|---|---|
| 2,565,057 A | 8/1951 | Ainsworth et al. | |
| 2,571,104 A | 10/1951 | Benedict | |
| 2,595,605 A | 5/1952 | Petty | |
| 2,602,041 A * | 7/1952 | Brown et al. | |
| 2,964,406 A | 12/1960 | Strandskov et al. | |
| 3,094,460 A | 6/1963 | De Boer et al. | |
| 3,132,994 A | 5/1964 | Duffin et al. | |
| 3,281,331 A | 10/1966 | Bergkvist | |
| 3,317,404 A | 5/1967 | Prave et al. | |
| 3,318,867 A | 5/1967 | Jahnke | |
| 3,376,339 A | 4/1968 | Svanholm | |
| 3,413,398 A | 11/1968 | Weddle | |
| 3,494,832 A | 2/1970 | Florent et al. | |
| 3,679,742 A | 7/1972 | Umezawa et al. | |
| 3,687,810 A | 8/1972 | Kurihara et al. | |
| 3,929,571 A | 12/1975 | Kubota et al. | |
| 4,308,346 A | 12/1981 | Niwano | |
| 4,444,883 A | 4/1984 | Brown et al. | |
| RE32,455 E | 7/1987 | Hamill et al. | |
| 4,870,158 A | 9/1989 | Karol et al. | |
| 4,912,036 A | 3/1990 | Cichanowicz et al. | |
| 5,147,441 A | 9/1992 | Megeed et al. | |
| 5,510,242 A | 4/1996 | Blais et al. | |
| 5,894,018 A | 4/1999 | Davila et al. | |
| 5,929,299 A | 7/1999 | Ikeda et al. | |
| 5,952,313 A | 9/1999 | Carlson | |
| 6,368,847 B1 | 4/2002 | Line et al. | |
| 6,579,696 B1 | 6/2003 | Shekhani et al. | |
| 6,719,973 B1 | 4/2004 | Ding et al. | |
| 7,070,992 B2 | 7/2006 | Baum et al. | |
| 7,297,551 B2 | 11/2007 | Ding et al. | |
| 2003/0008355 A1 | 1/2003 | Harrison | |

FOREIGN PATENT DOCUMENTS

| | | |
|---|---|---|
| CN | 1120585 | 4/1996 |
| CN | 1384200 | 12/2002 |
| CN | 1583171 | 2/2005 |
| DE | 4227682 | 10/1993 |
| EP | 0173937 | 3/1986 |
| EP | 0173944 | 3/1986 |
| EP | 0265127 | 4/1988 |
| EP | 0328256 | 8/1989 |
| EP | 1529784 | 5/2005 |
| FR | 1096978 | 6/1955 |
| GB | 742589 | 12/1955 |
| GB | 755370 | 8/1956 |
| GB | 757246 | 9/1956 |
| GB | 782926 | 9/1957 |
| GB | 874188 | 8/1961 |
| GB | 974334 | 11/1964 |
| GB | 991602 | 5/1965 |
| GB | 1064300 | 4/1967 |
| GB | 1119668 | 7/1968 |
| GB | 2154606 | 9/1985 |
| JP | 53053680 | 5/1978 |
| JP | 53095991 | 8/1978 |
| JP | 54128501 | 10/1979 |
| JP | 55081584 | 6/1980 |
| JP | 60184100 | 9/1985 |
| JP | 60199398 | 10/1985 |
| JP | 63180860 | 7/1988 |
| JP | 1296998 | 11/1989 |
| JP | 4009304 | 1/1992 |
| JP | 4071478 | 3/1992 |
| JP | 4200388 | 7/1992 |
| JP | 8098678 | 4/1996 |
| JP | 8126495 | 5/1996 |
| JP | 9121884 | 5/1997 |

(Continued)

OTHER PUBLICATIONS

"Diaion® and Sepabeads® Synthetic Adsorbents" Mitsubishi Chemical Corporation (Copyright 2000.).

*Primary Examiner* — Tekchand Saidha
*Assistant Examiner* — MD. Younus Meah
(74) *Attorney, Agent, or Firm* — Michael Best & Friedrich LLP

(57) ABSTRACT

The invention is related to the process of fermentation with production strain *Bacillus polymyxa* for industrial production of antibiotic polymyxin B with yield from 1.8 to 2.8 g/l of filtrate of fermentation broth at temperature 28° C., pressure 40–70 kPa, aeration from 0.4 to 1 vvm, concentration of dissolved oxygen minimal 60%, maintenance of pH and optimal concentration of glucose and ammonium ions.

12 Claims, No Drawings

FOREIGN PATENT DOCUMENTS

| | | |
|---|---|---|
| JP | 2003259861 | 9/2003 |
| KR | 920008386 | 9/1992 |
| MD | 2078 | 1/2003 |
| MD | 2285 | 10/2003 |
| RU | 2113471 | 6/1998 |
| RU | 2113472 | 6/1998 |
| RU | 2115721 | 7/1998 |
| RU | 2132880 | 7/1999 |
| RU | 2139348 | 10/1999 |
| RU | 2158758 | 11/2000 |
| RU | 2203317 | 4/2003 |
| RU | 2213779 | 10/2003 |
| RU | 2214453 | 10/2003 |
| RU | 2218395 | 12/2003 |
| RU | 2223313 | 2/2004 |
| RU | 2223499 | 2/2004 |
| RU | 2225441 | 3/2004 |
| WO | 01/27628 | 4/2001 |

* cited by examiner

PROCESS FOR THE PREPARATION OF POLYMYXIN B EMPLOYING (PAENI) BACILLUS POLYMYXA

This application is a U.S. national phase application filing of International Patent Application No. PCT/SK2007/0050011, filed 21 May 2007, which claims priority to Slovak Patent Application No. PP 0090-2006, filed 15 Jun. 2006. The entire contents of each of the foregoing applications are incorporated herein by reference.

TECHNICAL FIELD

Invention is regarded to process of fermentation with production strain *Bacillus polymyxa* which produces polymyxin B.

BACKGROUND ART

The polymyxins belong to cyclic polypeptide antibiotics. The first notes about polymyxin as antibiotics comes from a period of fifty years from the last century. We divided polymyxins to A, B, C, D, E, F, M, S and T.

Polymyxin B represents a mixture of polymyxins B1, B2, B3 and B1I. The composition of polymyxins listed above and representation of amino acid units and fatty acids are as follows:

| Antibiotic | L-Threonine | L-Leucine | D-Fenylalanine | L-DBA | Fatty acid |
|---|---|---|---|---|---|
| Polymyxine B1 | 2 | 1 | 1 | 6 | MOA |
| Polymyxine B2 | 2 | 1 | 1 | 6 | MHA |
| Polymyxine B3 | 2 | 1 | 1 | 6 | Octanoyl |

DBA—2,4 diaminobutyrate
MOA—6-methyloktanoyl
MHA—6-methylheptanoyl

Polymyxin B is an antibiotic for human purposes, effective for Gram-negative rods, especially for *Shigela, Salmonela, Escherichia* and *Klebsiela*. It is not effective for *Proteus, Providentia, Bactericides* and *Serratia* and generally for fungi and Gram-positive bacteria. It is not absorbed by digestion, very weakly is absorbed to tissues, does not penetrate to the cells and it is secreted by the kidney.

The production microorganism: *Bacillus polymyxa*

Published patents relating to polymyxin B fermentation field by using strain *Bacillus polymyxa* are as follows:

1. U.S. Pat. No. 2,595,605

In the patent is described the composition of fermentation media. The addition of corn flour increased production of antibiotics from 1200 IU/ml to 1800-2000 IU/ml for 88 hours of cultivation, what is equal to a concentration of polymyxine 0.251 g/l, measured by HPLC. It is not mentioned which type of polymyxin it was.

2. U.S. Pat. No. 2,571,104

In the patent is described the influence of mutagenesis by UV light to cells of a production strain, whereby an isolate with 5-times higher production of polymyxin in comparison with parental strains is obtained. This isolate has name *Bacillus polymyxa* NRRL B-719, it is stable, its production characteristic is kept till the 40th generation, utilized the following carbon sources: glucose, xylose, starch, and as a suitable source of amino acids are corn-steep, peanut flour, soya flour, yeast extract, ground corn. In the patent is described the way of one batch feed of fermentation media at 72 hour of cultivation. Production yield of polymyxin is 1000 IU/ml after 116 hours of cultivation, which is equal to a concentration of 0.125 g/l.

3. U.S. Pat. No. 2,602,041

The patent described improved isolation process and killing cells of production strain by using 0.4% solution of chloroform.

According the patent search was find patent of Russia, related to process of polymyxine fermentation M and Japanese patents, related to polymyxine fermentations F, T1, S1.

DISCLOSURE OF THE INVENTION

The invention is related to the process of fermentation to reach production of antibiotic polymyxin B at a concentration of 2.8 g/l in laboratory fermenter with a volume of 80 l.

Production strain *Bacillus polymyxa* growth on slant agar, which has a main source of amino acids is soya flour. Bacterial suspension of production strain inoculated to Petri dishes with agar is cultivated in thermostat at 28° C. from 68 to 72 hours. In laboratory scale fermentation is run on a rotary shaker at stirring 240 rpm and temperature 28° C. The best isolates reach production approximately 1.8 g polymyxin B/l of filtrate from fermentation broth, measured by HPLC method after 30 hours of cultivation with suitable representation of unit polymyxins and with minor unknown product till 3%.

The inoculum in volume from 1 to 10% from volume of fermentation media is cultivated in inoculation fermenter. Inoculation medium, which composition should be equal with production medium is inoculated from 0.05% to 1% of bacterial suspension prepared on slant agar. The cultivation run for aseptic conditions from 18 to 24 hours under pressure from 40 to 50 kPa, aeration from 0.4 to 1 vvm and intensive agitation. Good inoculum is characterized: pH in range from 5.2 to 6.5 depends from broth which was used, moving short rods of production strain in exponential faze of growth curve.

The vegetative inoculum is seeded into sterile production media in volume from 1 to 10%. Fermentation conditions of polymyxin in production fermenter are: pressure from 40 to 70 kPa, aeration from 0.5 to 0.8 vvm, regulation of pH in a range from 5.2 to 5.6 by ammonium hydroxide solution, maintenance of concentration of glucose in a range from 0.5 to 2.5 g/l by continual feeding of glucose solution (60%), maintenance of concentration of ammonium ions in a range from 0.3 to 0.6 g/l by feeding of ammonium sulphate solution (20%), in case of foaming feeding of vegetable or synthetic antifoam agent. The whole process of fermentation runs under aseptic conditions. The concentration of dissolved oxygen is maintained above 30% during fermentation. The source of amino acids in fermentation medium are soya flour in concentration from 0.5 to 2.0%, wheat flour from 0.5 to 5%, wheat bran in concentration 5 till 15 g/l, corn-steep from 0.2 to 2.5%, further ingredients are glucose in concentration from 0.5 to 5%, ammonium sulphate from 0.1 to 1%, potassium dihydrophosphate from 0.01 to 0.1%, heptahydrate of magnesium sulphate from 0.01% to 0.1%, heptahydrate of iron sulphate from 0.001 to 0.01%, microelements and vitamins B in minimal concentrations. Fermentation is finished after acute increase of dissolved oxygen and stop utilization of glucose.

Listed procedure of fermentation process with production strain *Bacillus polymyxa* in middle scale volumes till 35 l of fermentation broth is used to take from 40 to 55 hours. Attained yield of polymyxine in filtrate of fermentation broth are in a range from 1.8 to 2.8 g of polymyxine/l of filtrate measured by HPLC method. This fermentation technology, the composition of fermentation medias and yield of polymyxin has not been registered invention yet.

Description of the strain: *Bacillus polymyxa*
Morphology:—gram-positive sporulated rods
Optimal pH of cultivation: from 5 to 7
Utilization of carbon source: good utilization of glucose
Utilization of amino acids from organic sources: soya flour, wheat flour wheat bran, corn steep
Optimal temperature of cultivation: 28±1° C.
Representation of polymyxins: B1, B1I, B2, B3

EXAMPLES OF EMBODIMENTS

Example 1

Vegetative inoculum is cultivated in 30 l laboratory fermenters during 18 till 20 hours under temperature 28° C., agitation from 200 to 300 rpm in inoculation broth with following composition: corn-steep liquid 20 g/l, glucose 50 g/l, ammonium sulphate 4 g/l, calcium carbonate 3 g/l, natrium chloride 1 g/l, pH of the broth is adjust before sterilization on 6.8 till 7.0. Inoculum is seeded with 0.1% of bacterial suspension of production strain *Bacillus polymyxa* prepared in slant agar. Fermentation of polymyxine run in laboratory fermenter with working volume 35 l of fermentation broth with following composition: wheat flour 12 g/l, soya flour 12 g/l, glucose 15 g/l, ammonium sulphate 3 g/l, monopotassium phosphate 0.3 g/l, calcium carbonate 1 g/l, pH of the broth is adjust before sterilization on 6.8 till 7.0. Fermentation broth is inoculated with 4% of vegetative inoculum and cultivated at 28° C., aeration from 21 to 28 l, pressure 40 till 60 kPa. Intensity of agitation during fermentation is regulated to have saturation of dissolved oxygen in broth minimal 60%. The cultivation is feeding with solution of glucose from 22 hour of cultivation and maintained in concentration of glucose from 1.5 to 2.5 g/l and with solution of ammonium sulphate to maintained ammonia ions from 0.3 to 0.5 g/l. When the pH of the broth decreases to 5.2 ammonium hydroxide is added to keep pH in a range from 5.2 to 5.6. Fermentation broth is antifoaming by vegetable oil and synthetic antifoam agent. Under these conditions production strain *Bacillus polymyxa* reach a yield 2.3 g of polymyxine per 1 l of filtrate of fermentation broth.

Example 2

The vegetative inoculum is cultivated in 30 l laboratory fermenters during 20 hours in inoculation broth with following composition: corn-steep liquid 20 g/l, glucose 20 g/l, ammonium sulphate 4 g/l, calcium carbonate 3 g/l, natrium chloride 1 g/l, under same conditions as in example 1.

Fermentation of polymyxin run in laboratory fermenter with working volume 35 l of fermentation broth with following composition: wheat flour 40 g/l, wheat bran 10 g/l, glucose 15 g/l, ammonium sulphate 4 g/l, monopotassium phosphate 0.3 g/l, calcium carbonate 3 g/l, pH of the broth is adjust before sterilization on 6.8 till 7.0. Fermentation broth is inoculated with 4% of vegetative inoculum and cultivated at 28° C. and cultivated under same conditions as in example 1. Under these conditions production strain *Bacillus polymyxa* reach a yield 2.4 g of polymyxin B per 1 l of filtrate of fermentation broth.

Example 3

The vegetative inoculum is prepared in two steps. Inoculation broth in both steps has following composition: corn-steep, ammonium sulphate, calcium carbonate and glucose, pH of the broth is adjusted before sterilization on 6.8 till 7.0. At first the inoculum is seeded with 1.0% of bacterial suspension of production strain *Bacillus polymyxa* prepared in slant agar. It is cultivated in Erlenmeyer flask on rotary shaker at temperature 28° C. and agitation 240 rpm during 14 till 18 hours. The vegetative inoculum in amount 0.1% is seeded into second step and cultivated in laboratory fermenter 14 till 18 hours. The vegetative inoculum in amount 4% is seeded into fermentation broth with following composition: wheat flour 12 g/l, soya flour 12 g/l, glucose 15 g/l, ammonium sulphate 3 g/l, monopotassium phosphate 0.3 g/l, calcium carbonate 1 g/l, pH of the broth is adjusted before sterilization to 6.8 till 7.0. Fermentation in working volume 35 l takes 44 till 54 hours under same conditions as in example 1 and 2. Fermentation is stopped when utilization of glucose is stopped, biosynthesis of polymyxin B is stopped and the concentration of dissolved oxygen in fermentation broth rapidly increases. Under these conditions production strain *Bacillus polymyxa* reach a yield 2.8 g of polymyxin B per 1 of filtrate of fermentation broth.

INDUSTRIAL APPLICABILITY

Production strain *Bacillus polymyxa* produces antibiotic polymyxin B during fermentation in industrial production in concentration from 1.8 to 2.8 g per l of filtrate of fermentation broth.

The invention claimed is:

1. A method of cultivation of a production strain of *Bacillus polymyxa* comprising, cultivating the strain in a fermentation broth at a temperature of 28° C. in a fermenter with agitation and aeration of the fermentation broth, while maintaining the pH during cultivation in a range of 5.3 to 5.6, adding a solution of glucose during cultivation to maintain a glucose concentration in a range of 0.5 to 2.5 g/l adding ammonium ions during cultivation to maintain an ammonium ion concentration in a range of 0.3 to 0.6 g/l, and filtering the fermentation broth after 44 to 56 hours of cultivation to provide a concentration of polymyxin B in the filtrate of 1.8 to 2.8 g/l as measured by HPLC method.

2. The method according to claim 1 wherein the fermentation broth has a start concentration of phosphate of 50 to 80 mg/l.

3. The method according to claim 1 wherein the fermentation broth has a start concentration of glucose of 10 to 20 g/l.

4. The method according to claim 1 wherein the fermentation broth has a start concentration of ammonium ions of 0.5 to 1.5 g/l.

5. The method according to claim 1 wherein during fermentation the pH is maintained by adding a solution of ammonium hydroxide.

6. The method according to claim 1 wherein the fermentation broth is seeded with a vegetative inoculum in an amount from 1 to 10% of the fermentation broth volume.

7. The method according to claim 1 wherein during fermentation the intensity of agitation is regulated to provide a saturation of dissolved oxygen in the broth of at least 60%.

8. The method according to claim 1 wherein the fermentation broth is seeded with an inoculum and the inoculum is seeded with a bacterial suspension in amount from 0.05% to 1% of the inoculum volume.

9. The method according to claim 8 wherein the inoculum is cultivated in a procedure comprising a single seeding step.

10. The method according to claim 6, wherein the inoculum is cultivated in a procedure comprising a single seeding step.

11. The method according to claim 8 wherein the inoculum is cultivated in a procedure comprising two seeding steps.

12. The method according to claim 6, wherein the inoculum is cultivated in a procedure comprising two seeding steps.

\* \* \* \* \*